(12) United States Patent
Bischoff et al.

(10) Patent No.: US 7,187,965 B2
(45) Date of Patent: Mar. 6, 2007

(54) CARDIAC RHYTHM MONITORING DEVICE

(76) Inventors: Edward T. Bischoff, 2213 Belmont Pl., Metairie, LA (US) 70001; Gary D. Menszer, 425 Iona St., Metairie, LA (US) 70005

( * ) Notice: Subject to any disclaimer, the term of this patent is extended or adjusted under 35 U.S.C. 154(b) by 669 days.

(21) Appl. No.: 10/156,978

(22) Filed: May 29, 2002

(65) Prior Publication Data

US 2003/0023178 A1 Jan. 30, 2003

Related U.S. Application Data

(60) Provisional application No. 60/294,301, filed on May 29, 2001, now abandoned.

(51) Int. Cl.
*A61B 5/0452* (2006.01)

(52) U.S. Cl. ................................... 600/515

(58) Field of Classification Search ......... 600/515–518
See application file for complete search history.

(56) References Cited

U.S. PATENT DOCUMENTS

| | | | |
|---|---|---|---|
| 4,422,459 A | 12/1983 | Simson | |
| 4,763,663 A | 8/1988 | Uphold et al. | |
| 4,781,200 A | 11/1988 | Baker | |
| 4,803,625 A | 2/1989 | Fu et al. | |
| 4,952,928 A | 8/1990 | Carroll et al. | |
| 5,086,772 A | 2/1992 | Larnard et al. | |
| 5,111,396 A | 5/1992 | Mills et al. | |
| 5,228,449 A | 7/1993 | Christ et al. | |
| 5,289,824 A | 3/1994 | Mills et al. | |
| 5,333,616 A | 8/1994 | Mills et al. | |
| 5,442,940 A | 8/1995 | Secker et al. | |
| 5,474,574 A * | 12/1995 | Payne et al. | ................ 607/7 |
| 5,522,396 A | 6/1996 | Langer et al. | |
| 5,577,510 A | 11/1996 | Chittum | |
| 5,749,900 A * | 5/1998 | Schroeppel et al. | ........... 607/4 |
| 5,902,250 A | 5/1999 | Verrier et al. | |
| 6,144,837 A | 11/2000 | Quy | |
| 6,922,584 B2 * | 7/2005 | Wang et al. | ............... 600/515 |
| 2002/0065473 A1 | 5/2002 | Wang et al. | |
| 2002/0143266 A1 * | 10/2002 | Bock | .................... 600/518 |

* cited by examiner

*Primary Examiner*—George R. Evanisko
(74) *Attorney, Agent, or Firm*—Phelps Dunbar L.L.P.

(57) ABSTRACT

The present invention is a cardiac rhythm-monitoring device, which allows patients to perform a preliminary screening for supraventricular arrhythmia. The device detects beat-to-beat heart rhythms (i.e. the R—R interval between individual heart beats) and performs a screening test to determine if there are indications of arrhythmia. The test looks for variance in the R—R interval that is outside of the normal range, either using a pre-constructed chart based upon general population studies to determine the normal range of variance or using normal distribution analysis of the patient's own heart rhythm to determine the normal range of variance for determining irregular heartbeats, and if there are multiple irregularities within the sensed time frame, the patient is warned of potential supraventricular arrhythmia. By sensing both electrical impulses form the heart and mechanical responses to the heartbeat, the device may augment its analysis.

3 Claims, 10 Drawing Sheets

Figure 1 CRMD
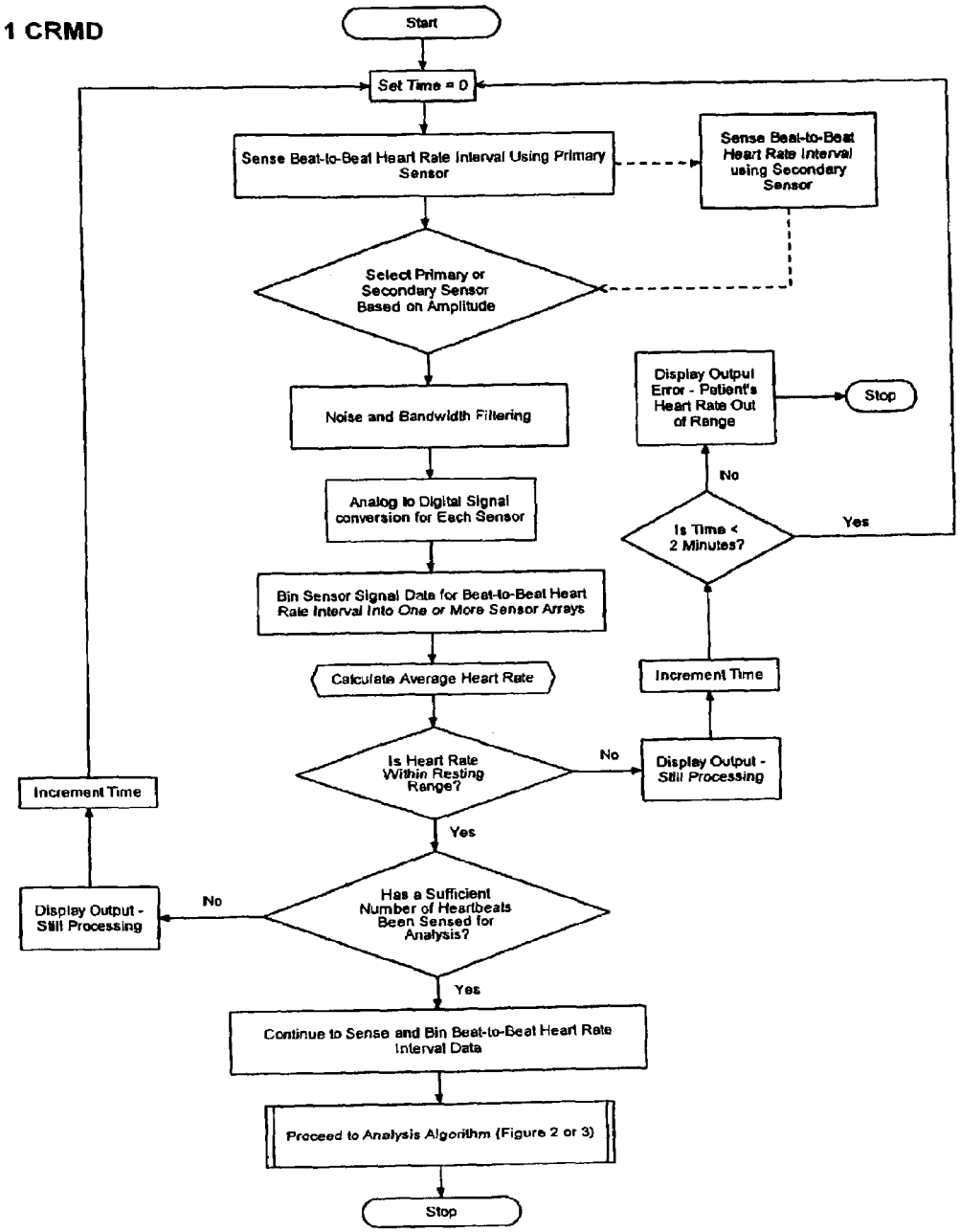

Figure 2 CRMD
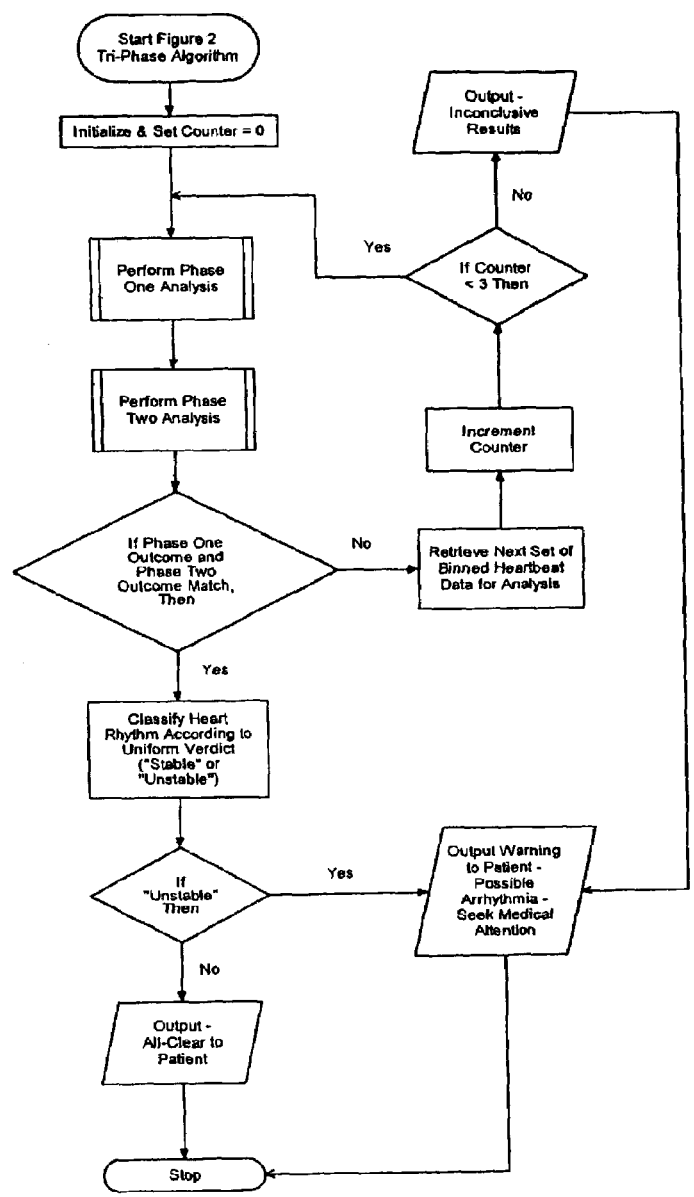

Figure 3 CRMD
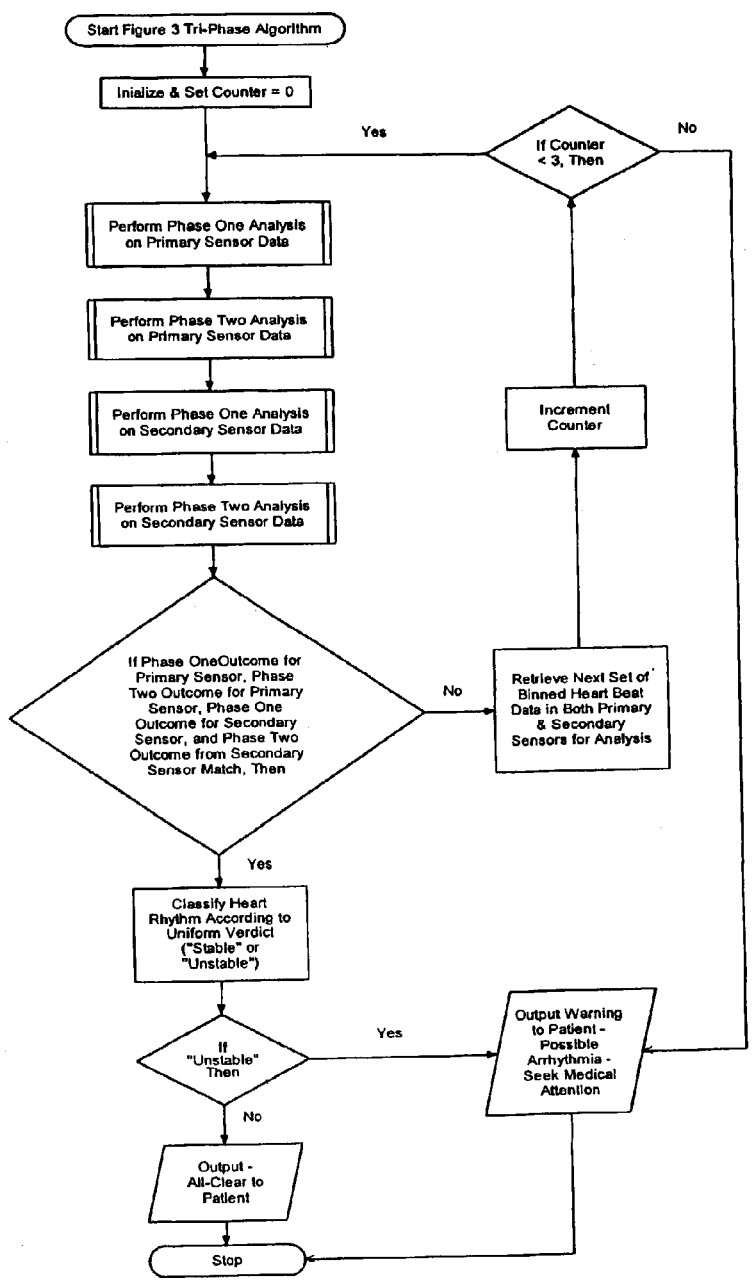

Figure 4.1 CRMD
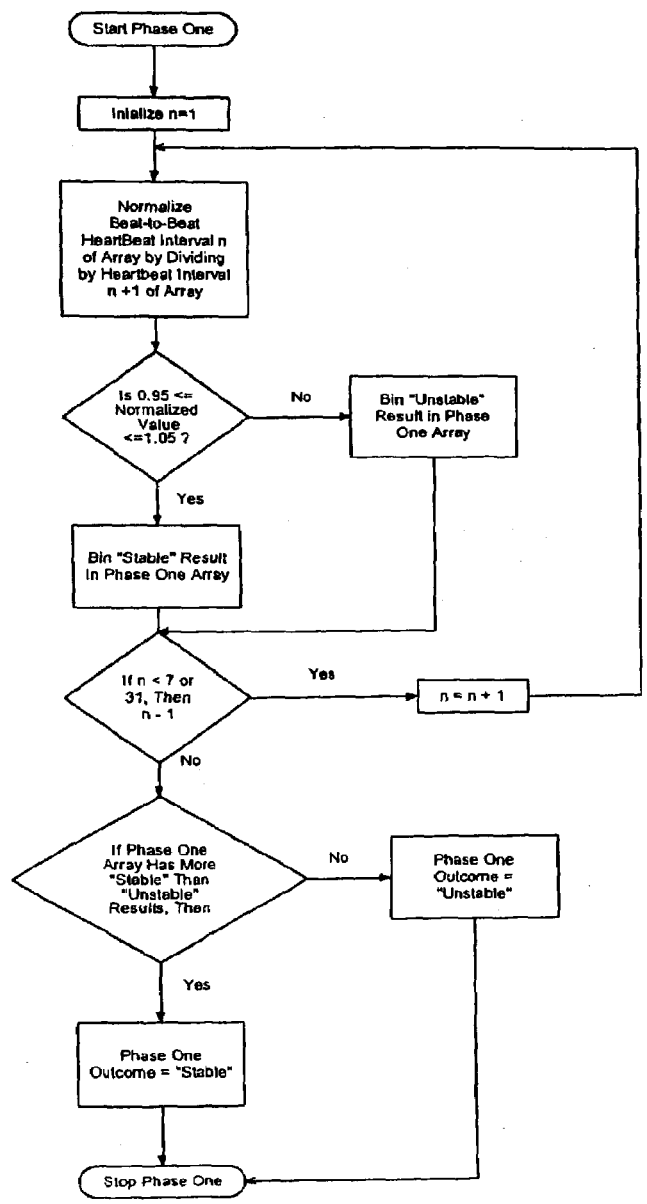

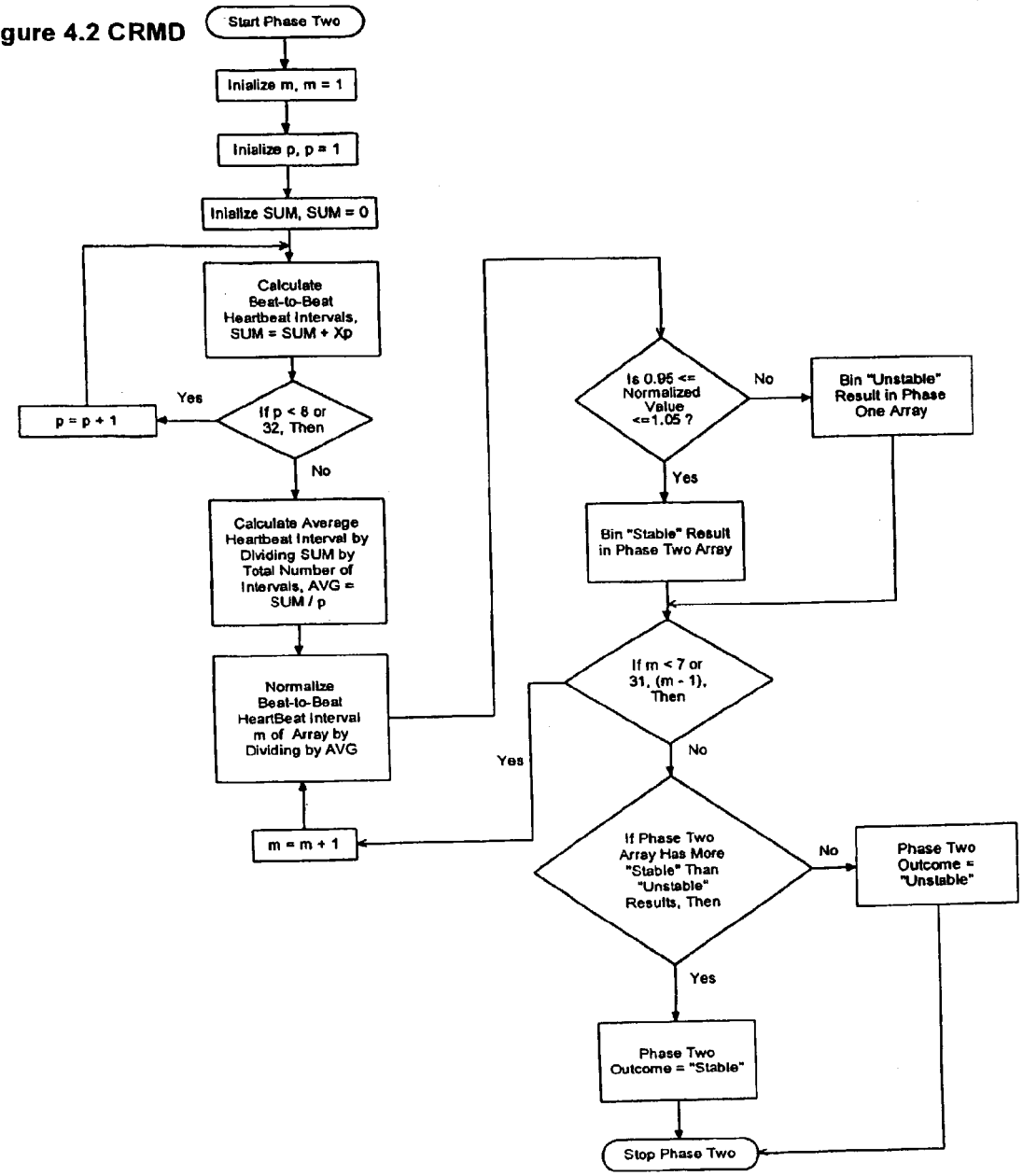
Figure 4.2 CRMD

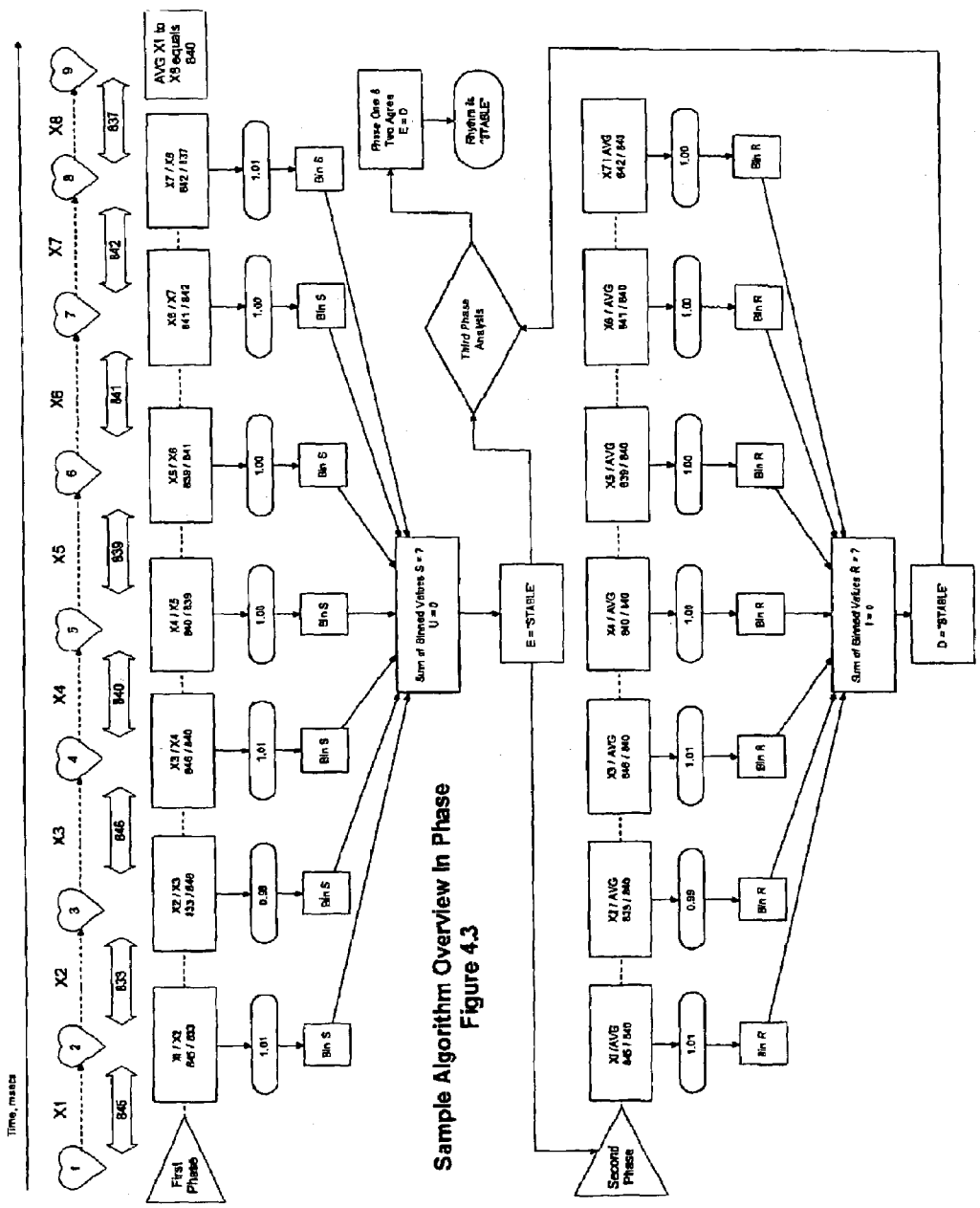
Sample Algorithm Overview In Phase
Figure 4.3

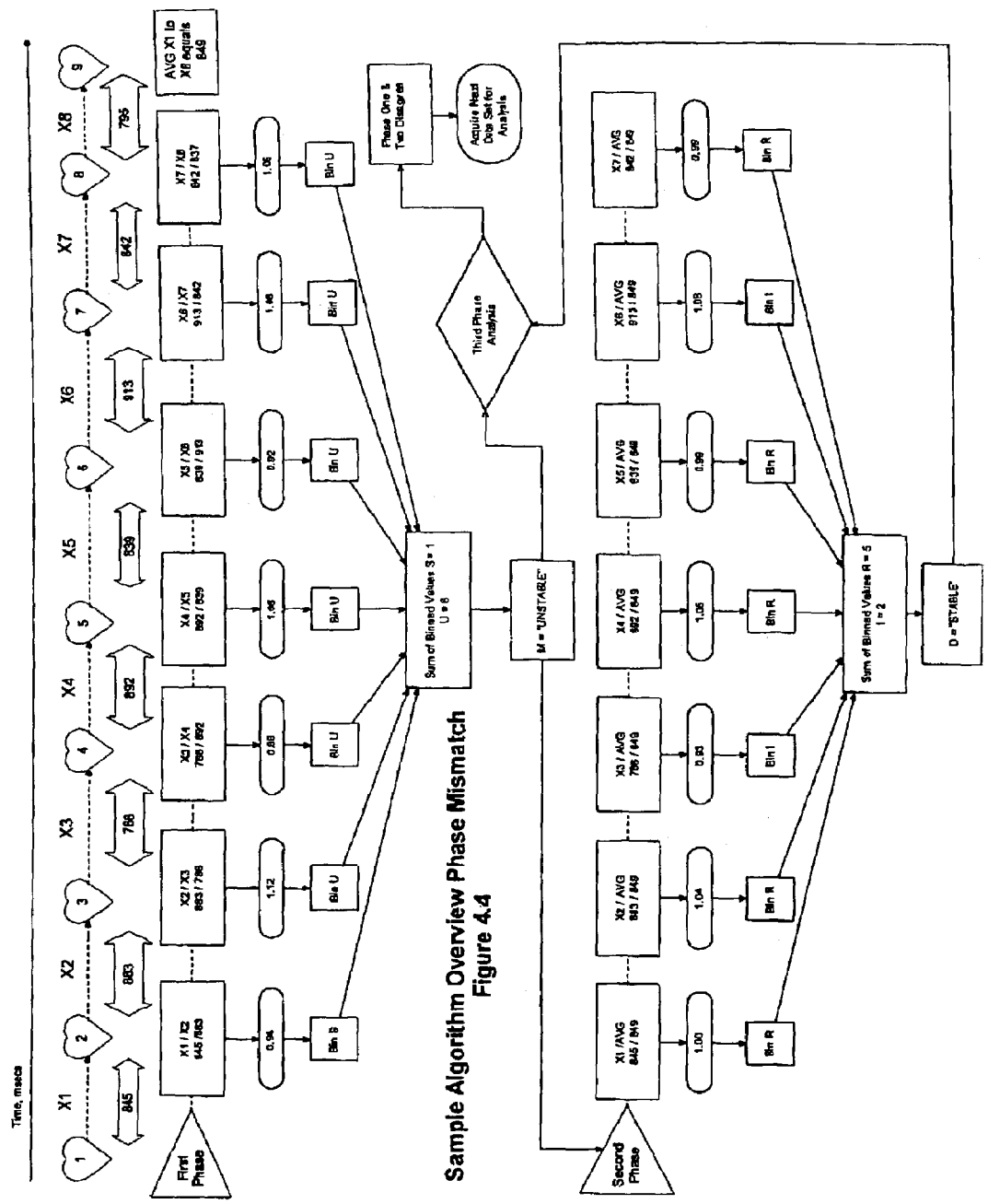

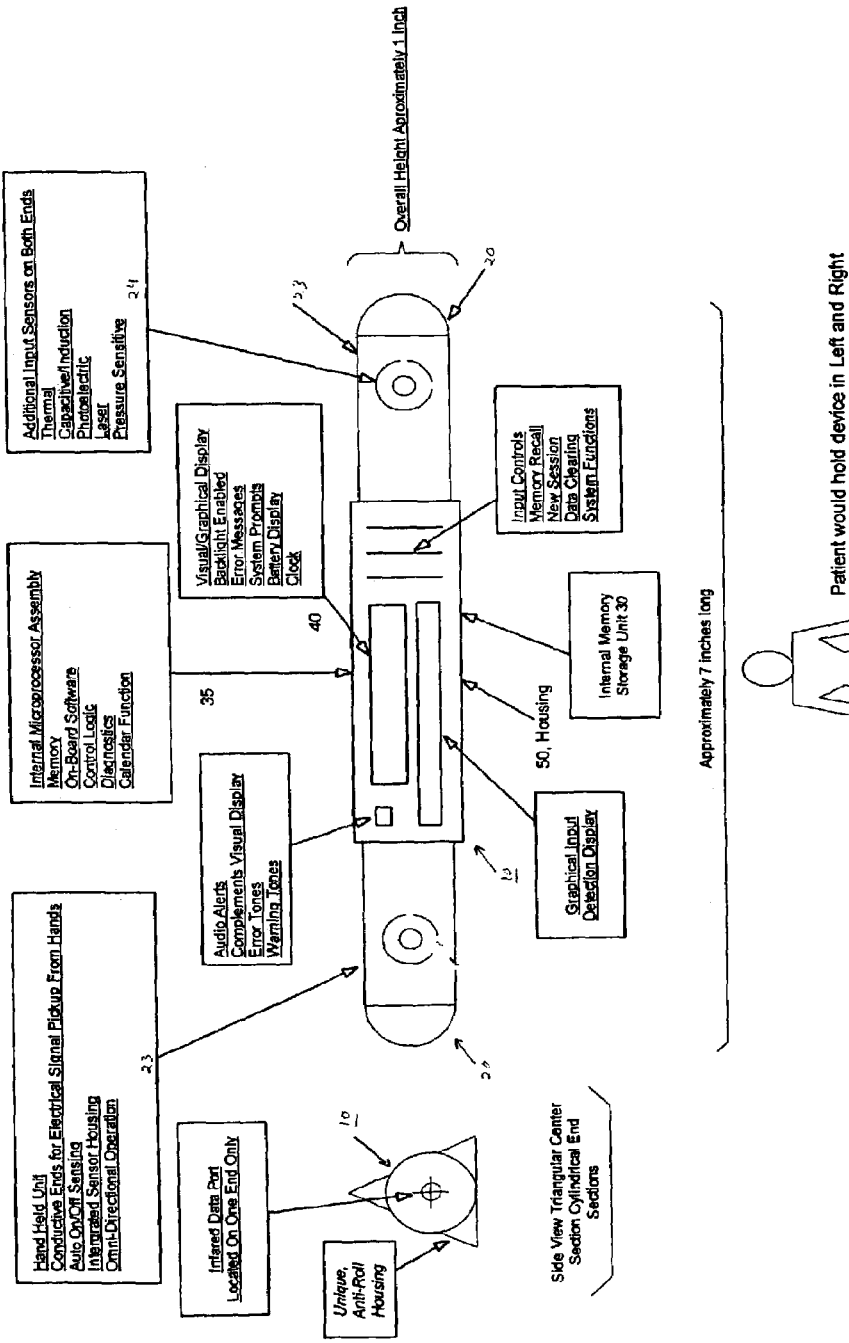
Figure 5.1

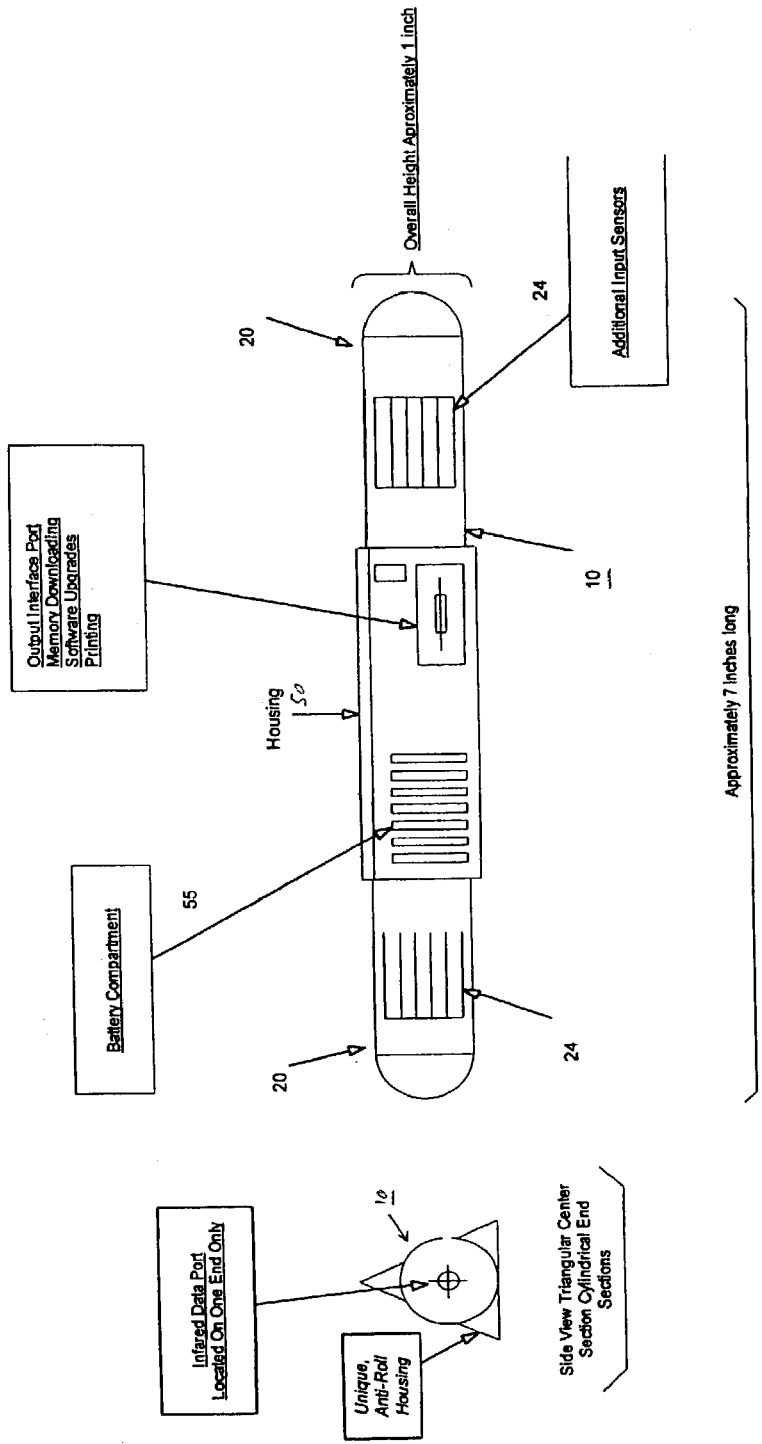

CARDIAC RHYTHM MONITORING DEVICE

This application claims the benefit of U.S. Provisional Application No. 60/294,301, FILING DATE May 29, 2001, now abandoned.

BACKGROUND OF THE INVENTION

Supraventricular arrhythmia is a particular type of electrical disturbance of the rhythm of the heart. It is an arrhythmia originating in the upper chambers of the heart, which can lead to an irregular, abnormal heartbeat. Supraventricular arrhythmia is a fairly common occurrence, and as people get older, their chance of experiencing supraventricular arrhythmia will typically increase. Supraventricular arrhythmia itself is not an immediately life-threatening condition. Current research, however, has revealed that supraventricular arrhythmia predisposes a patient to such life threatening conditions as stroke, cardiomyopathy, and congestive heart failure. Consequently, it is important for doctors to be able to detect supraventricular arrhythmia as early as possible, since the earlier that supraventricular arrhythmia is diagnosed and treated, the greater the chance that the arrhythmia or its dangerous side effects can be treated, reducing the risks of stroke, cardiomyopathy, and congestive heart failure. Furthermore, it is important to be able to monitor the arrhythmia over time, since duration is an important factor in evaluating the health risks associated with supraventricular arrhythmia and ongoing monitoring also allows doctors to regulate the amount of medication that patients take as treatment for supraventricular arrhythmia.

Unfortunately, patients often will not even realize that they are experiencing supraventricular arrhythmia, since secondary symptoms may not appear or may be difficult to recognize. The standard technique for detecting arrhythmias employs an electrocardiogram ("ECG"), which uses several electrical leads attached to the patient's chest to monitor the patient's heart during a visit to the doctor's office (where the ECG machine is located). An ECG is a medical diagnostic device that produces a fairly detailed readout of the patient's heart rhythm, which a medical professional may interpret in order to evaluate how a patient's heart is functioning during the visit to the doctor's office. An ECG often does not monitor a patient's real-time beat-to-beat rhythm, however; instead, it may process the patient's heart rhythm over discrete time intervals (such as 5 seconds) to provide a "snapshot" heart rhythm output for interpretation by a medical expert. Consequently, it may be difficult for even medical professionals to detect supraventricular arrhythmia using an ECG. A real-time, beat-by-beat analysis of the patient's heart rhythm would allow for more accurate assessment of a patient's heart rhythm in order to detect the presence of an arrhythmia.

Furthermore, supraventricular arrhythmia is often an intermittent, sporadic condition, such that the use of an ECG during a visit with a doctor may not reveal any irregularity in the heart rhythm, since the patient may not be experiencing the arrhythmia at that time. In such a case, regular (periodic) or continuous monitoring of the patient's heart rhythm would be better able to detect supraventricular arrhythmia. Once supraventricular arrhythmia has been detected, regular monitoring is also recommended in order to determine the duration of the arrhythmia, since sustained supraventricular arrhythmia lasting more than 24 to 48 hours greatly increases the chance of a blood clot forming that could cause a stroke in the patient.

Regular monitoring would also allow for adjustment of the dosage of medications treating the supraventricular arrhythmia (or the secondary symptoms) based upon the patient's daily condition. Once an arrhythmia has been detected, doctors often prescribe blood-thinning drugs (anti-coagulants), such as Coumadin® (Warfarin Sodium), in order to reduce the chances of blood clot formation, or anti-arrhythmia medications, in order to stabilize the heart rate. Unfortunately, both the blood-thinning drugs and the anti-arrhythmia medications may have side effects, some of which can be medically serious. Therefore, doctors may prefer daily monitoring of the patient's heart rhythm for supraventricular arrhythmia, so that they may lower the dosage of drugs that the patient takes as the arrhythmia subsides (as opposed to the current practice of maintaining the same dosage level between doctor visits, which are typically spaced six months apart). This may reduce the side effects experienced by the patient. A device that a patient could use to monitor their heart rhythm, searching for signs of supraventricular arrhythmia, would address all of these needs. Since a patient would operate such a device, it should be simple, portable, convenient, low-cost, self-contained, non-invasive, and automatically assess the patient's likelihood of arrhythmia.

The present invention of the Cardiac Rhythm Monitoring Device ("CRMD") is designed to perform all of these functions. It is not designed to be used exclusively by doctors as the primary device for sensing, detecting, diagnosing, or classifying arrhythmias. Rather, the CRMD allows for periodic monitoring of the rhythm of a patient's heart, warning the patient if it detects potential supraventricular arrhythmia activity. This can be useful when a doctor suspects that a patient has experienced intermittent supraventricular arrhythmia, but the ECG does not record any abnormal heart rhythms during the visit to the doctor's office. The CRMD can provide a preliminary warning of the possibility of a serious supraventricular arrhythmia, alerting the patient to see a doctor for a more thorough analysis of their rhythms. If the CRMD detects supraventricular arrhythmia for over a 24-hour period, for example, the patient has a greater need for medical attention than if the duration of the arrhythmia is shorter. And, the CRMD can be used in conjunction with blood-thinning medications or anti-arrhythmia medications to regulate the dosage according to the condition of the patient's heart rhythm.

The CRMD may be used in a discrete, periodic manner, or it may be used to continuously monitor the patient's heart rhythm. In the first embodiment, the patient, as described above, would typically use the CRMD periodically. In the second embodiment, however, the CRMD could also be used continuously, which would be especially useful for detecting intermittent supraventricular arrhythmia. In that case, the patient would wear the CRMD continuously throughout the day. This would allow for continuous, uninterrupted monitoring of the patient's heart rhythm, such that the CRMD would be able to warn the patient immediately whenever it detects a potential supraventricular arrhythmia. The patient would then be able to seek prompt medical treatment from medical professionals, who could apply confirmatory tests to verify an arrhythmia and provide the appropriate level of treatment to the patient. For this type of continuous monitoring to be effective, however, the CRMD must not interfere substantially with patient's lifestyle (or else the patient will not wear it). Thus, convenience factors (such as small size, light-weight, and unobtrusive configuration) will be incorporated into the design of the device.

SUMMARY OF THE INVENTION

The Cardiac Rhythm Monitoring Device ("CRMD") is a simple, user-friendly medical device designed to be operated by a patient, without the need for extensive training. It monitors the patient's heart rhythm and determines if a patient is likely experiencing supraventricular arrhythmia. The CRMD may be used periodically, for regular checks of a patient's heart rhythm, or it may be used in a continuous, uninterrupted manner, for constant monitoring of a patient's heart rhythms. When used by a patient under the guidance and supervision of medical professionals, the CRMD can aid in the detection of intermittent supraventricular arrhythmia, can assist in determining the duration of the arrhythmia, and can assist in customizing the appropriate dosage of medication to fit the patient's specific needs.

To effectively detect supraventricular arrhythmia, an analysis of the patient's beat-to-beat heart rate must be performed. The CRMD monitors a patient's beat-to-beat heart rate over a period of time, and analyzes the patient's heart rhythm to determine if it indicates that the patient is experiencing supraventricular arrhythmia. The CRMD is not designed to perform the extensive and detailed tests which would be required in order to develop a final diagnosis concerning the patient's heart rhythm (that would, for example, specifically classify the type of arrhythmia being experienced). Instead, the CRMD is designed to primarily serve a preliminary screening function. Thus, if the CRMD indicates that a patient may be experiencing supraventricular arrhythmia, the patient is directed to seek medical attention so that medical professionals may perform more extensive tests to diagnosis the specific problem and to develop an appropriate treatment regimen.

The CRMD will often be used only periodically. For example, the CRMD may be used approximately once per day by the patient in order to check if the supraventricular arrhythmia lasts more than 24 hours. Arrhythmia is more dangerous if it lasts more than 24 hours, since prolonged arrhythmia encourages blood clotting which could, in turn, lead to stroke or other complications. Thus, if repeated, periodic uses of the CRMD indicated that the patient's arrhythmia has lasted more than 24 hours, the patient may need to seek immediate medical attention.

Furthermore, once a patient has been diagnosed with supraventricular arrhythmia, the doctor will often prescribe blood-thinning medication, such as Coumadin® (Warfarin Sodium), in order to reduce the likelihood of blood clot formation, or anti-arrhythmia medications, in order to restore the patient's heart rate to a more normal rhythm. Unfortunately, these medications may have fairly dangerous side effects themselves, which could become life-threatening. For example, patients on blood-thinning medications are at an increased risk of bleeding. Therefore, it is preferable to use these blood-thinning medications only for as long as necessary (i.e. during supraventricular arrhythmia activity) and only in the lowest effective dosages, in order to limit the risk of bleeding to the patient. The CRMD may be used to monitor the patient's heart rhythm on a daily basis in order to allow for medical personnel to determine the appropriate dosage of medication to be used by the patient while the supraventricular arrhythmia continues, and to determine when the arrhythmia has ended and the drugs are no longer required.

The CRMD device is essentially comprised of one or more sensors, which detect the R—R interval signal of the patient's heart rhythm (i.e. the actual beat-to-beat heart rate); a memory storage means, such as one or more computerized arrays, which stores the sensed beat-to-beat heart rhythm over a period of time in order to allow for proper analysis to determine if a warning regarding arrhythmia is warranted; and a processing unit, which executes an algorithm to analyze the sensed heart rhythm searching for indications of arrhythmia.

The primary input (from the sensors) to the processing unit consists of the measured R—R interval of the patient's heart rhythm. This is a beat-to-beat input, indicating the amount of time between each individual heartbeat. Most commonly, the CRMD senses the R—R interval using two conductive electrodes, one contacting on the left side of the patient's body and one contacting on the right side of the patient's body, in order to sense the electrical current flow through the patient's heart. This is a non-invasive means for sensing the patient's beat-to-beat heart rhythm, making the CRMD user-friendly. When the patient's heart beats, the electrical impulse of the heart is transmitted throughout the patient's body. It is this very weak electrical signal, emanating from the patient's heart and indicating potential contraction of the heart as a beat, which becomes the primary input signal. The two electrodes of the CRMD receive this weak electrical signal from the patient's body. The signal is then typically amplified, digitized, and normalized before being transmitted to the processing unit for analysis. Although other sensing mechanisms (such as pulse oximeters, thermistors, optical electrodes, peak blood flow (pulse) and pressure sensors, capacitance/induction sensors, infrared/photoelectric sensors, and impedance sensors) could be used to measure the R—R interval, conductive electrode sensors provide an effective combination of ease-of-use, convenience, cost-effectiveness, and accuracy.

The processing unit uses the input data from the sensors to determine if the patient is likely experiencing supraventricular arrhythmia by analyzing the regularity of the patient's heart rhythm. A heart rhythm will have some variation, even in a perfectly healthy, normal person. For a normal, healthy person, however, the variance is limited. So for instance, general population studies have indicated that the typical variance in time between heart beats for a healthy, normal heart is less than 125 milliseconds beat-to-beat. Extrapolating from this evidence, it stands to reason that if the signal from a patient indicates a variance outside of the normal range (i.e. more than a variance of 125 milliseconds between heart beats based on the example study), then there is a potential problem that could indicate arrhythmia. More specifically, the analysis performed by the processing unit would compare each R—R interval between heart beats to the average R—R interval for the patient. For a normal, healthy heart, the difference (i.e. variance) between each particular R—R interval and the calculated average R—R interval is less than or equal to 125 milliseconds; any variance greater than 125 milliseconds (above or below the average R—R interval calculated for the patient) would be indicative of a potential problem. Each such event is a potential irregular heart beat outside of the normal R—R interval variance range (based on general population studies). This type of analysis essentially uses a pre-constructed data table based on general population studies to determine the appropriate criteria for classifying individual heart beat intervals as irregular. Obviously, the precise criteria could vary depending upon the study used as the basis for comparison (and a variance of 125 milliseconds is merely an example).

Alternatively, the processing unit could analyze the patient's sensor data for irregular heart beats using a statistical approach based upon normal distribution analysis of the patient's own heart rhythm. Again, the processor would be searching for irregular heart beats which are outside of the normal range of variance typically seen in human hearts, but this form of analysis effectively builds a data table to determine the appropriate criteria for classifying individual heart beat intervals as irregular instantaneously, using the patient's own individual heart rhythm to shape the criteria rather than basing the criteria on more general factors from studies of broader populations. Thus, this approach has the benefit of being customized to the particular patient. In this statistical approach, each sensed beat-to-beat heart beat interval is normalized using a standard normalization technique (such as dividing each interval by the average interval, for example). This allows normal distribution pattern analysis techniques to be utilized to identify heart beat intervals which are irregular and to indicate an unstable heart rhythm. Only normalized heart beat intervals at the extreme range of the normal distribution curve indicate irregularity, so for instance, those normalized values falling outside of the range of 0.95 to 1.05 might be classified as irregular.

It is, however, fairly common for even healthy persons to experience an occasional variance in the interval between heartbeats which is slightly outside of the normal range. In other words, occasionally even a normal, healthy heart will produce an extra beat or skip a beat. One or more brief events outside a patient's normalized R—R interval variance range may not indicate supraventricular arrhythmia. Consequently, the CRMD will analyze the patient's beat-to-beat heart rhythm over some period of time, 10–60 seconds for example, or over a certain number of heart beats, with a sample data set typically ranging from 8 to 32 heart beats, to determine if there is a sustained irregularity that may indicate supraventricular arrhythmia. If the CRMD detects several irregular heartbeats with varying R—R intervals in the appropriate time frame (for example 3 or more within a minute) or a statistically significant number of normalized heartbeats indicating irregularity within a sensed data set, then that may be a strong indication of supraventricular arrhythmia. If the CRMD is used for an even longer period of time (greater than the base period), its analysis should become even more accurate, since the calculated R—R interval baseline will become more accurate as additional heart beats are factored into the calculations, allowing the CRMD software to more effectively identify irregular heart beats.

In order to further improve the analysis performed by the CRMD, additional inputs related to the patient's beat-to-beat heart rate might optionally be used in addition to the primary sensor input. For example, the CRMD may optionally sense for peak blood flow, using a pulse pressure sensor, and/or for pulse oxygenation, using an optical sensor to monitor changes in the oxygenation of the patient's blood, in order to compare these mechanical/physiological indications of the patient's heart rhythm to the electrical R—R interval indication of the patient's heart rhythm. Such optional secondary inputs would serve as a check, verifying the accuracy of the electrical R—R interval input data and screening out false data (such as electromagnet noise from the environment around the patient). The secondary inputs would also provide more detailed information about the patient's heart rhythm for analysis, since the amount of lag time between the electrical signal (generated by the heart and sensed by the electrodes of the CRMD) and the mechanical/physiological (blood flow) responses also changes when a patient is experiencing supraventricular arrhythmia. The measured delay between the electrical signals and the mechanical signals can also assist in the detection of a patient experiencing arrhythmia.

In addition to the required elements of one or more sensors for detecting the patient's beat-to-beat heart rhythm, a temporary memory block to store heart beat (R—R interval) data for the required duration needed to analyze the patient's heart rhythm, and a processing unit to analyze the data to determine if there are indications of supraventricular arrhythmia, there are also some additional features for the CRMD. First, the CRMD will require a power source to operate. While it could be plugged into a wall outlet to run off of centralized power, an independent, portable power source, such as one or more batteries, would be more convenient. A casing or housing, which could protect the processing unit from potentially damaging events and could protect the patient from electrical shock, would also make the CRMD a more durable and safe device.

In addition, an output unit may be provided so that the patient may receive indication of the test results from the CRMD (although the CRMD may be designed so that it plugs into an external output device as well). For convenience, the output unit may be integrated into the CRMD device itself. For example, the output unit may indicate a warning by illuminating a red light when a problem is indicated. Or, a more sophisticated LCD-type screen could provide the patient with more detailed information concerning the test results and the recommended course of action. The output device need not be visual either. It could, for example, provide an audible alarm, or it could utilize a voice synthesizer to communicate with the patient. Further, the full output unit does not need to be incorporated within the CRMD. Instead, the CRMD could transmit its results to another, separate device for output to the patient or medical professionals. For example, the patient could download the results onto their personal computer, which would display the output in a form that the patient could understand. Or, the results from the processing unit could be transmitted over phone lines or over the Internet to the doctor's office, so that medical professionals may review the output results and discuss the information with the patient.

Another optional element, which may be added to the CRMD, would be additional non-volatile memory storage space. Then, for example, the CRMD (used in a continuous monitoring format) could log a patient's heart rhythm over a longer period of time; say 24 hours, so that a doctor could review the actual beat-to-beat heart rhythm of the patient while diagnosing the patient's condition. Or, the CRMD (used in a periodic manner) could record the time and date of each test by the patient along with the results, so that a doctor could chart a patient's status over a longer period of time, in between monthly visits for example. Thus, the CRMD could be used as an additional source of information about the patient's heart rhythm as medical professionals diagnosis the patient's condition, develop an appropriate treatment regimen, and monitor the patient's progress under the treatment regimen.

In the most typical arrangement of the CRMD configured for periodic testing, the CRMD would be housed in a casing with integrated handles. Each of the handles would have a conductive electrode to sense the patient's beat-to-beat (R—R interval) heart rhythm. Optionally, this version of the CRMD could also have secondary sensors incorporated within it. For example, besides the conductive electrodes in the handles, which directly sense the heart's electrical impulses, the handles could also have a finger pulse oximeter incorporated to measure the patient's mechanical/physiological (blood flow) responses. The sensor data would be transmitted to the processing unit, typically located in the housing between the two handles, and the results from the processing unit would be displayed on a LCD-type screen located atop the central portion of the housing, in between the two handles. Thus, the patient would grip the handles for a period of time, typically 10–60 seconds, and would then receive an indication concerning their heart rhythm.

Alternatively, the CRMD could be configured for continuous usage by the patient. In the most typical arrangement of the CRMD configured for continuous monitoring, the patient would wear two sensor bands, on their wrists, for example. The sensor bands would contain the conductive electrodes for detecting the heart's electrical impulses, and could also incorporate a pulse pressure-sensing device to monitor the secondary, mechanical/physiological responses of the patient. This data would then be transmitted to the processing unit, which would typically be located in a housing worn on a belt in the manner of a Walkman™, for example. The housing would also usually include some sort of output device, such as a warning alarm and/or warning lights, to notify the patient when a problem has been detected. An LCD-type screen could also be included, to provide additional details to the patient after the initial warning. Furthermore, one of the sensor bands may also include the housing for the processor and other microelectronics, including an integrated output display device.

The object of this invention is to provide either periodic or continuous monitoring of a patient's beat-to-beat heart rhythm. It is another object of this invention to provide preliminary detection of supraventricular arrhythmia. It is still another object of this invention to warn a patient of potential supraventricular arrhythmia. It is yet another object of this invention to allow for detection of intermittent supraventricular arrhythmia. It is yet another object of this invention to screen out noise and singular events which do not indicate supraventricular arrhythmia. It is yet another object of this invention to store data concerning the patient's heart rhythm. It is yet another object of this invention to provide information concerning the patient's heart rhythm and/or to suggest a course of action to the patient. It is yet another object of this invention to detect the duration of a supraventricular arrhythmia event. It is yet another object of this invention to allow for a patient's medication dosage to be regulated and adjusted based upon their detected heart rhythm. It is yet another object of this invention to be sufficiently simple, low cost, and durable so that patients may monitor their own heart rhythm for potential supraventricular arrhythmia. It is yet another object of this invention to be convenient and unobtrusive so that the CRMD may be worn continuously by a patient without interfering unduly with the course of their daily activities.

These and other objects and uses will be apparent to persons skilled in the art field. Further, a person skilled in the art field will appreciate that there are several different sensing devices, processing units, memory storage units, output units, power supply sources, case housing, configurations, and methods of analyzing the patient's heart rhythm for possible arrhythmia which would function in the present invention. While several examples are described herein, the present invention is not limited to these examples, which are provided merely for illustrative purposes. Rather, the present invention includes these specific examples and any equivalents. And, although the present invention is described primarily as a tool for patients to monitor their own heart rhythm for signs of arrhythmia, it is to be understood that the device is not limited to such use.

BRIEF DESCRIPTION OF THE DRAWINGS

FIG. 1 is a flowchart of the basic steps performed by the CRMD.

FIG. 2 is a flowchart of the analysis algorithm for detecting supraventricular arrhythmia using only one sensor input regarding the patient's beat-to-beat rhythm.

FIG. 3 is a flowchart of the more complex analysis algorithm for detecting supraventricular arrhythmia using secondary sensor input regarding the patient's mechanical/physiological responses in addition to the primary sensor input regarding the patient's electrical responses.

FIG. 4.1 is a flowchart of Phase One of the analysis algorithm of the preferred embodiment, wherein the patient's heartbeat data is normalized by dividing by subsequent heartbeat data and then analyzed for stability.

FIG. 4.2 is a flowchart of Phase Two of the analysis algorithm of the preferred embodiment, wherein the patient's heartbeat data is normalized by dividing by the average heartbeat and then analyzed for stability.

FIG. 4.3 is a flowchart of the base algorithm for detecting supraventricular arrhythmia with the R—R interval stability index indicating a triple phase logical agreement of the representative R—R interval sample synchronization.

FIG. 4.4 is a flowchart of the base algorithm for detecting supraventricular arrhythmia with the R—R interval stability index indicating a sample phase mismatch.

FIG. 5.1 is a graphical illustration of one embodiment of the CRMD configured for periodic use.

FIG. 5.2 is a graphical illustration of another view of the CRMD embodiment configured for periodic use.

DETAILED DESCRIPTION OF PREFERRED EMBODIMENTS

Figure 6:
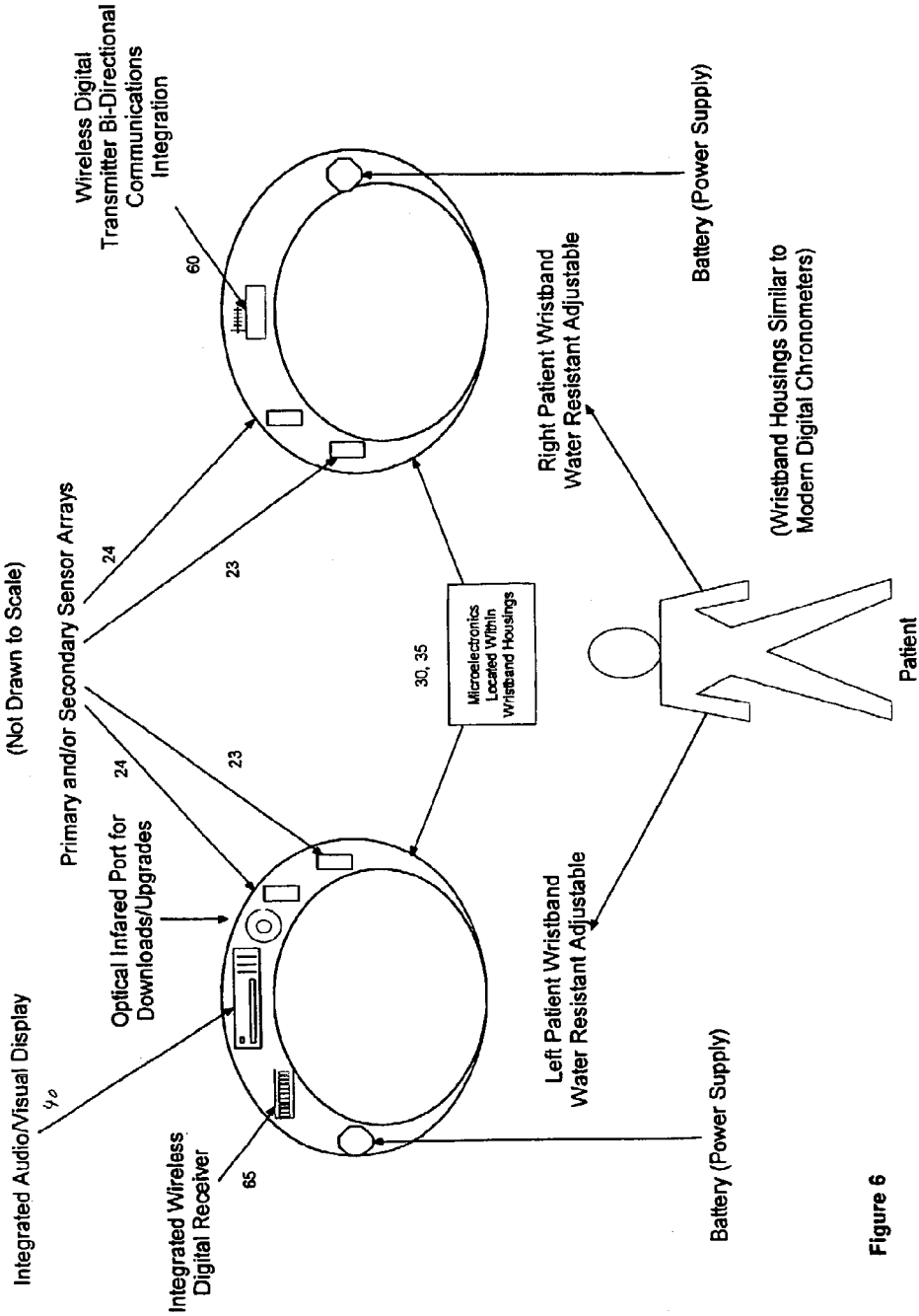
FIG. 6 is a graphical illustration of one embodiment of the CRMD configured for continuous monitoring of a patient's heart rhythm.

The CRMD, generally designated by the numeral 10, is a medical instrument that executes a particular procedure to determine if a patient's heart rhythm indicates possible supraventricular arrhythmia. More specifically, in the preferred embodiment the CRMD 10 executes the procedure shown generally in FIG. 1 for determining if a patient's heart rhythm has indications of supraventricular arrhythmia. First, the CRMD 10 senses the patient's beat-to-beat heart rhythm, measuring the R—R interval between heartbeats. This data is temporarily stored (typically in a computerized array) for use in the detection algorithm. The input data or the results may also be stored for analysis later by medical professionals. One of the analysis algorithms shown generally in FIGS. 2 or 3, depending upon the number of sensor inputs available, is used to determine if the patient should be warned about supraventricular arrhythmia. If there is only one sensor input regarding the patient's beat-to-beat heart rhythm, then the algorithm shown in FIG. 2 is used; if there are two or more sensor inputs, however, then the more complex algorithm of FIG. 3 is used to determine whether to warn the patient of the potential for arrhythmia. The output data from the algorithm is then displayed, either warning the patient of potential arrhythmia or signaling a normal heart rhythm.

As is discussed above, there are primarily two different physical variants of the CRMD 10. The first variant of the CRMD 10 is used periodically or episodically to determine if a patient is experiencing supraventricular arrhythmia at specific points in time. Although this variant of the CRMD 10 may be configured in many different ways, FIGS. 5.1 and 5.2 illustrate the preferred embodiment. The CRMD 10 shown in FIGS. 5.1 and 5.2 has two handles 20, which are to be grasped by the patient, one in each hand. Located on the surface of the handles 20 are one or more sensors used to detect the patient's beat-to-beat heart rhythm (i.e. the R—R interval between heart beats). In the preferred embodiment, each handle 20 has a conductive electrode sensor 23 to detect the electrical impulses generated by the patient's heart. Sensors that detect heartbeats by sensing the electrical impulse generated by the heart are typically more accurate and precise, so they are preferred. Other types of sensors, which detect the body's mechanical response to the heartbeat (such as blood flow changes), could also be used, so long as they provide accurate results.

The sensor does not have to detect the patient's beat-to-beat rhythm at any particular location. Any appropriate location is acceptable, depending upon the configuration of the CRMD 10. In the preferred embodiment, the sensors are located on the handles 20 for ease of use. Optional supplemental sensors 24 could also be included to provide additional data. For example, when the primary sensor detects electrical impulses representing each heart beat, the secondary sensor will typically detect corresponding mechanical/physiological reactions keyed to the heartbeat. In that case, the secondary sensor could be a finger pulse oximeter, which could be located on the underside of one of the handles 20 and which would detect the changes in the blood flow caused by the beating of the patient's heart. Also, peak blood flow (pulse) pressure sensors could be located on the other handle 20, to detect pressure changes at one of the patient's pulse points cause by the beating of the patient's heart. Any sensor, which detects mechanical responses, would be appropriate, so long as it is accurate. In the preferred embodiment shown in FIG. 5.1, the primary sensor is a pair of conductive electrodes 23, while two secondary supplemental sensors 24 are used, a pulse oximeter and a peak blood flow (pulse) pressure sensor.

The beat-to-beat signal detected by the one or more sensors is often amplified and normalized in this preferred embodiment before being transmitted to a temporary memory storage unit 30 and on to the processing unit 35 for analysis using one of the acceptable methods for detecting likely arrhythmia based upon sensed heart rhythm. The input data from the one or more sensors is typically transmitted via wire/circuit board etching. The temporary memory storage unit 30 (typically an array) stores the heart beat data over the appropriate time frame, typically 10–60 seconds, for the processing unit 35 to analyze the patient's heart rhythm. The processing unit 35 performs the detection algorithm, shown in either FIG. 2 or FIG. 3 (depending upon the number of input signals sensed), to determine if there are indications of supraventricular arrhythmia based upon the patient's beat-to-beat heart rhythm.

Depending upon the results of the analysis, the processing unit 35 may transmit output data to the output display unit. In the preferred embodiment of FIG. 5.1, the output display unit is an LCD-type screen 40 located atop the central portion of the housing 50, which informs the patient of the outcome of the test, warning the patient if a potential arrhythmia is detected. Other possible output display units could be merely a flashing light to warn the patient, an audible alarm to warn the patient, or a digitized voice. The CRMD 10 also includes a power supply source 55 to run the various functions of the device. Although any type of power supply source may be used (including a plug for use in a standard wall socket or solar power cells), a battery is used in the preferred embodiment because it provides dependable power without any restrictions to movement. In the preferred embodiment, a standard (over the counter) type of battery is used. The functional elements of the CRMD 10 are all contained within a housing 50, which protects the functional elements from harm and provides for convenient and safe handling of the CRMD 10. The preferred embodiment of the CRMD 10 shown in FIG. 5.1 is approximately seven inches in length, so that it may be conveniently carried by a patient. And in this preferred embodiment, the CRMD 10 employs a housing 50 with a triangular cross-section, in order to prevent the device from rolling when it is placed upon a flat surface.

The second variant of the CRMD 10 monitors the patient's heart rhythm continuously. For continuous monitoring, it must be worn by the patient over extended periods of time; so for this type of use, the CRMD 10 must be configured in a convenient, unobtrusive manner. Although there are numerous possible ways to configure the CRMD 10 for continuous monitoring of the patient's heart rhythm, the preferred embodiment of this configuration is illustrated in FIG. 6. In this embodiment, the sensors are typically worn as wristbands, one on each of the patient's wrists. The sensor units are approximately the size of a wristwatch, and in the preferred embodiment, the primary sensors are conductive electrodes 23 that contact the patient's skin and sense the electrical impulse generated by the patient's heart. Additional, secondary supplemental sensors 24 that monitor the patient's mechanical responses, such as a peak blood flow (pulse) pressure sensor or a pulse oximeter, may be include within the wristbands. Furthermore, while the data could be transmitted to the processing unit 35 via wires (which would restrict the patient's freedom of movement), the preferred embodiment utilizes a wireless transmitter 60. If the sensors detect mechanical responses, then the sensors will need to be worn on pulse points on the patient's body. If the sensors rely exclusively on electrical impulse detection, then location is not as critical. For example, if two conductive electrodes 23 are the sole sensor means, then they may be placed anywhere about the patient's body so long as one conductive electrode 23 is located on each side of the patient's body.

The processing unit 35, temporary memory storage unit 30, any additional memory storage unit, output display unit 40, and power supply source 55 may be incorporated within a housing 50 which can be worn by the patient on a belt, in the manner of a Walkman™. The processing unit 35/memory unit 30 also includes a receiver 65 for the wireless transmission of data from the sensor bands in this preferred embodiment. It is also possible to incorporate the processor 35, memory storage unit 30, receiver 65, and the output display unit 40 within the housing for one of the sensor units. In the preferred embodiment for example, shown in FIG. 6, the processor 35, memory storage unit 30, data receiver 65, and output display unit 40 are incorporated within one of the sensor units for convenience.

For continuous monitoring, convenience factors are important, so the CRMD 10 in this embodiment is designed to be compact and lightweight, to have a useable power source life span of at least 24 hours, and to be worn in an unobtrusive manner that does not interfere substantially with daily activities, etc. Although it is configured differently, since this second variant must be worn over some period of time, it functions in the same essential way to monitor the patient's heart rhythm. If the algorithm determines that the signal inputs from the sensors indicate that the patient is experiencing a potential arrhythmia, the processing unit will transmit an output signal to warn the patient.

While the above detailed description has focused on the two primary versions of the preferred embodiment of the physical form of the CRMD 10, the remainder of this detailed description section will focus on the method employed internally within the CRMD 10 to analyze a patient's heart rhythm in order to detect likely arrhythmia. The actual determination of likely arrhythmia and the decision of whether to warn the patient is performed by applying a detection algorithm to analyze the patient's beat-to-beat heartbeat rhythm pattern. In the preferred embodiment, the algorithm is set forth as computer-operated software, with an electronic processing unit analyzing the sensed beat-to-beat heartbeat data of the patient in order to search for signs of arrhythmia. No specific software or algorithm is required, so long as it performs the overall function of determining if there is a sustained pattern of heartbeat intervals outside of the normal physiological range of variance, which is indicative of arrhythmia. Indeed, the specific software and/or algorithm may be dependent upon several factors, including the number of sensors available for detecting the patient's beat-to-beat heartbeat rhythm, the amount of memory space available for storing the sensed heartbeat data and/or the intermediate determinations of whether a particular interval indicates an irregularity, and the chosen method of analysis and level of sensitivity/safety factor desired in the warning process.

Although there are several variants of the present invention, all of which are generally included within the scope of this description, the preferred embodiment of the method employed within the CRMD 10 is shown in FIGS. 1, 2, and 3. FIG. 1 is a flowchart which generally illustrates the initial portion of the preferred embodiment of the arrhythmia detection algorithm, while FIGS. 2 and 3 are alternative versions of the second portion (termed the analysis portion) of the arrhythmia detection algorithm. FIG. 2 illustrates the analysis portion of the preferred embodiment of the arrhythmia detection algorithm when only one heart beat sensor is utilized, whereas FIG. 3 illustrates the analysis portion of the preferred embodiment of the arrhythmia detection algorithm when there is a primary sensor and at least one secondary sensor.

Furthermore, as has been briefly explained above, while there are several possible methods for analyzing beat-to-beat heartbeat intervals in order to determine if a patient is likely experiencing an arrhythmia and should, therefore, seek medical attention, in the preferred embodiment a tri-phase analysis based on statistical analysis of the specific patient's heart rhythm is utilized. This tri-phase analysis is demonstrated in both FIGS. 2 and 3, with FIGS. 4.1 and 4.2 further detailing the first and second phases of the analysis process. It is understood, however, that this is in no way intended to limit the scope of this invention. Rather, the analysis portion of the algorithm may be any of various possible alternative methods available, depending upon the specific needs of the design. By way of example, either of the Phase One or Phase Two analysis could be used alone in place of the tri-phase analysis of the preferred embodiment, although accuracy may be reduced. Similarly, a pre-constructed table based upon data from a general population study could be used to determine whether a patient's beat-to-beat heartbeat intervals were outside of the normal variance range. A person skilled in the art field will appreciate that these and other analysis techniques would apply as alternatives to the tri-phase analysis set forth in the preferred embodiment, and this invention is intended to include all such variations. The preferred embodiment utilizes the tri-phase statistical analysis because it is patient specific and provides additional accuracy, reducing the likelihood of false positives.

Turning now to the drawings of the preferred embodiment in more detail, FIG. 1 illustrates the initial portion of the arrhythmia detection algorithm. In the preferred embodiment, the CRMD 10 is configured so that it is activated automatically when the patient grips both conductive electrodes 23. Alternative means for activating the CRMD 10, such as an on/off power switch or button or even operating the device on a solar cell which automatically activates when there is sufficient light available to power the device, do exist and could also be used.

Regardless, the process begins by sensing the patient's beat-to-beat heartbeat intervals. Any of several types of reliable heart beat sensors could be used, including both electrical sensors and mechanical/physiological sensors, such as pulse oximeters, thermisters, optical electrodes, peak blood flow (pulse) and pressure sensors. In the preferred embodiment, the primary sensing means utilizes conductive electrodes 23 to detect the electrical impulses generated by the patient's heart in order to measure the patient's beat-to-beat heartbeat intervals. Optionally, depending upon whether the analysis portion of the arrhythmia detection algorithm (either FIG. 2 or FIG. 3) utilizes additional sensor input for additional accuracy and/or to provide back-up sensing capabilities, one or more secondary sensing means may also be utilized to detect the patient's beat-to-beat heartbeat rhythm. If additional, secondary sensors are employed, then another optional feature may be used to determine which of the several available sensor input signals should be treated as the primary sensor (rather than merely designating the primary sensor based upon general performance standards for the various sensors). If this optional step is included, then the sensor with the highest available stable input signal amplitude would be selected as the primary sensor, and the remaining sensors would be designated as secondary sensors.

Another optional feature (not shown in FIG. 1) would be to verify that both the electrical and mechanical/physiological signals roughly correspond. In this way, the CRMD 10 would preliminarily screen for outside sources of error. For example, if there is an electrical signal but no mechanical signal, this would tend to indicate a problem which may make the analysis algorithm operate inaccurately. It could, for instance, indicate that the patient has not properly gripped the CRMD 10, so that the mechanical sensors are unable to detect their heartbeat. Regardless, if there are disparate sensor readings from the various sensors, then an error message should be transmitted. The patient's heart rate is also optionally examined to ensure that it is within normal resting range, since the detection algorithm is formulated based upon the assumption of a patient at rest, and the accuracy of the analysis may be affected if the patient's heart rhythm is undergoing stress. Although there are several means for defining the normal resting heart rate range, which a person skilled in the art will be familiar with, in the preferred embodiment the normal resting range is defined as approximately between 35 to 220 beats per minute. If the patient's heart rate falls outside of the normal resting range, then an error message is displayed and additional heartbeats will continue to be sensed until either the patient's heart rate enters the normal resting range or a time limit (of two minutes in the preferred embodiment) expires.

Once the available sensors of the CRMD 10 are sensing the patient's beat-to-beat heartbeat intervals, noise and bandwidth filtering are generally applied in order to screen out any background electrical noise and interference. Typically, the filter is set to screen out any signals beyond the level of magnitude of the physiological range of the human heart. This reduces sources of external error, providing for a more accurate arrhythmia detection process. Then, the analog signals from the sensors (representing the patient's beat-to-beat heartbeat rhythm) are converted to digital signals, using a digitizer, for more efficient processing (utilizing a computerized processing means). The digital data from these signals are stored, so that the analysis algorithm (FIG. 2 or FIG. 3) can process the data and analyze the patient's beat-to-beat heartbeat intervals for indications of arrhythmia. In the preferred embodiment, the digital data for the patient's sensed beat-to-beat heartbeat interval rhythm is stored in a separate computerized array for each sensor. The data will continuously be sensed and stored in the one or more arrays so long as the patient is using the CRMD 10, but the analysis algorithm will take place using discreet sets of data within the arrays. The analysis algorithm will begin once a sufficient number of data points representing beat-to-beat heartbeat intervals for the patient have been collected in order to complete a set for analysis, although data will continue to be sensed and stored while the analysis algorithm is operating in case additional information is needed for later processing in Phase Three of the tri-phase analysis utilized by the preferred embodiment of the CRMD 10.

Typically, the minimum number of beat-to-beat heartbeat intervals required for a set for proper analysis is eight, since this provides a pattern with a statistically significant number of heartbeat intervals for an adequate level of accuracy. While slightly smaller data sets may be possible, they raise the risk of increasing errors beyond an acceptable level, resulting in an inordinate amount of false positives. Obviously, the larger the data set used for analysis, the more accurate the algorithm outcome is likely to be, as larger data sets reduce the effect of the occasional aberrant heartbeat and provide a broader picture of the patient's heart rhythm. In the preferred embodiment, the set has been enlarged to include thirty-two data points for increased accuracy.

Once the array has stored a sufficient number of heart beat data points for a set, the CRMD 10 begins the analysis portion of the arrhythmia detection algorithm, as shown in FIGS. 2 and 3 for the preferred embodiment. Both FIGS. 2 and 3 utilize generally the same basic analysis method, termed tri-phase analysis, to determine if there is a likely arrhythmia. FIG. 2 is simpler in that it includes only a single sensor and so the analysis only operates on a single set of data stored in a single array. FIG. 3 is quite similar to FIG. 2 in overall purpose, but involves some added complexity since it utilizes at least one secondary sensor data set in addition to the data set from the primary sensor.

The tri-phase analysis utilized in the preferred embodiment is only one of several methods for analyzing the patient's beat-to-beat heartbeat data for indications of arrhythmia. There are two primary types of algorithms which may be used. The more basic analysis technique would be to compare the patient's beat-to-beat heartbeat interval variance to a pre-constructed table based upon a general population study, in order to determine if each interval variance falls outside of the normal variance of time between heartbeats for a healthy person. So, for instance, the R—R interval of a particular heart beat would be compared to the average R—R interval between heartbeats for the patient over the data set, and the algorithm would keep track of the number of times that the variance exceeded the normal range for such variance as determined from a general population study, typically approximately 125 milliseconds based upon some current studies. Any variance outside of the normal range of variance would be a potential irregular heartbeat, and if a sufficient number of irregular heart beats were detected over a span of time, then that would indicate a potential arrhythmia and the CRMD 10 would warn the patient.

The second analysis technique uses individualized statistical analysis of the patient's own normalized heart rhythm, rather than some comparison to a general population study, in order to classify heartbeats as irregular, and then identifies heart rhythms with a sufficient number of irregular heartbeats as unstable and possibly indicative of arrhythmia. This is the preferred method of analysis, since it is patient-specific. In the preferred embodiment, the patient's heartbeat data is normalized and then standard normal distribution analysis is employed to determine if a particular heartbeat interval indicates an unstable heart rhythm which, when viewed as part of a pattern, could indicate arrhythmia. This is the method employed in the preferred embodiment. Actually, the preferred embodiment takes this technique a step further, utilizing multiple methods for normalizing the patient's heart rhythm in order to increase the accuracy of the analysis. This is certainly not required, and either the Phase One or Phase Two types of analysis could be utilized independently, along with other variations of normalization techniques familiar to persons skilled in the art field; but the tri-phase analysis algorithm provides an additional check, reducing the chances of incorrect outcomes.

Turning first to FIG. 2 and the simpler of the analysis algorithms, the basic structure of the algorithm involves three separate phases of analysis when there is only a single data set from a single heartbeat sensor. First, the preferred embodiment of the CRMD 10 runs the Phase One analysis shown in FIG. 4.1 on the patient's beat-to-beat heartbeat interval data set. Each sensed beat-to-beat heartbeat interval stored in the array is divided by the following sensed beat-to-beat heartbeat interval stored in the array (for example, the interval stored in the first array slot is divided by the interval stored in the second array slot), in order to normalize the data. Each normalized heartbeat interval is then considered using normal distribution analysis principles in order to determine if it should be classified as indicative of a stable or unstable trend. Although various criteria could be used to determine stability, depending for example on the level of accuracy and sensitivity desired for the CRMD 10, in the preferred embodiment, any normalized value which falls outside of the range from 0.95 to 1.05 would be deemed unstable. The overall outcome of Phase One is determined by comparing the number of "Stable" results to the number of "Unstable" results, with the Phase One overall outcome being set as "stable" if the number of stable results is greater than the number of unstable results and the Phase One overall outcome being set as "unstable" if the number of unstable results is greater than the number of stable results (and the data set should ideally be set to result in an odd number of results so that there is a definitive determination from the Phase One analysis).

Then, the preferred embodiment of the CRMD 10 performs the Phase Two analysis shown in FIG. 4.2 on the patient's beat-to-beat heartbeat interval data set. The average beat-to-beat heartbeat interval for the data set is calculated first, since this is the normalizing factor for Phase Two. Each sensed beat-to-beat heartbeat interval stored in the array is divided by the average beat-to-beat heartbeat interval for the data set, in order to normalize the data. Each normalized heartbeat interval is then considered using normal distribution analysis principles in order to determine if it should be classified as indicative of a stable or unstable trend. Although various criteria could be used to determine stability, depending for example on the level of accuracy and sensitivity desired for the CRMD 10, in the preferred embodiment, any normalized value which falls outside of the range from 0.95 to 1.05 would be deemed unstable. The overall outcome of Phase Two is determined by comparing the number of "Stable" results to the number of "Unstable" results, with the Phase Two overall outcome being set as "stable" if the number of stable results is greater than the number of unstable results and the Phase Two overall outcome being set as "unstable" if the number of unstable results is greater than the number of stable results (and the data set should ideally be set to result in an odd number of results so that there is a definitive determination from the Phase Two analysis, so the preferred embodiment does not examine the final stored heart beat interval).

Phase Three of the preferred embodiment, as shown on FIG. 2, compares the overall outcome for Phase One and Phase Two. If the Phase One outcome matches the Phase Two outcome, then the final overall result of the tri-phase analysis is this uniform verdict (i.e. if both Phase One and Phase Two indicate that the patient's heart rhythm is "stable," then the final overall result of the tri-phase analysis is "stable;" if both say "unstable," then the final overall result of the tri-phase analysis is "unstable"). If the final overall result of the tri-phase analysis is "stable," then the CRMD 10 outputs an all clear signal to the patient using the available output display device 40. If the final overall result of the tri-phase analysis is "unstable," then the CRMD 10 outputs a warning to the patient using the available output display device 40, indicating possible arrhythmia and advising the patient to seek medical attention in the preferred embodiment.

If, on the other hand, the Phase One outcome does not match the Phase Two outcome, then Phase Three will take the next data set (of 32 heartbeat intervals in the preferred embodiment) of the patient's beat-to-beat heart beat intervals stored in the array and re-run both the Phase One and Phase Two Analyses on the new data before again checking to see if the Phase One outcome matches the Phase Two outcome. This iterative approach will occur until either the Phase One outcome matches the Phase Two outcome, or until Phase Three has failed to produce a matching result after a pre-set number of iterations. In the preferred embodiment, if there is no match by the third iteration, then the CRMD 10 will output a signal indicating inconclusive results and warning of possible arrhythmia to the output display device 40. An example of the tri-phase analysis can be seen in FIGS. 4.3 and 4.4. FIG. 4.3 illustrates, using a data set of eight beat-to-beat heartbeat intervals as an example, the kind of analysis which would occur in the tri-phase analysis algorithm of FIG. 2 when both the Phase One outcome and the Phase Two outcome match (here providing a "Stable" result, for example). FIG. 4.4 illustrates, using a data set of eight beat-to-beat heartbeat intervals as an example, the kind of analysis which would occur in the tri-phase analysis algorithm when the Phase One outcome and the Phase Two outcome do not match, such that Phase Three must re-run the analysis on the next set of data in order to iteratively seek agreement.

It should be understood that either Phase One or Phase Two could be used alone, rather than as part of this tri-phase analysis of a patient's heart rhythm. Doing so would tend to reduce the accuracy of the analysis, however, and so to compensate it may be wise to increase the size of the data sets, to run multiple separate data sets using the specific analysis technique chosen, or to increase the sensitivity of the criteria for determining if a normalized heartbeat is stable or unstable. Furthermore, the pre-constructed chart technique discussed above could also be used alone or in tandem with either the Phase One or Phase Two technique for the analysis portion of the arrhythmia detection algorithm of the CRMD 10.

FIG. 3 illustrates a similar preferred embodiment of the analysis portion of the arrhythmia detection algorithm when multiple sensors are available, providing multiple simultaneous beat-to-beat heartbeat interval readings of the patient's heart rhythm. FIG. 3 assumes a primary sensor and a secondary sensor, such that there is a primary sensor array which stores the data for the beat-to-beat heartbeat intervals from the primary sensor and a secondary sensor array which stores the data for the beat-to-beat heartbeat intervals from the secondary sensor. In operation, the tri-phase analysis shown in FIG. 3 is very similar to that shown in FIG. 2, except that it is applied to both the data of the primary sensor array and the data of the secondary sensor array in order to provide additional accuracy.

In Phase Three, the final overall result is set to whichever classification (either stable or unstable) is uniformly held by the Phase One and Phase Two outcomes for both the primary and secondary data sets, unless there is not such uniform agreement, in which case the algorithm iteratively re-runs Phase One and Phase Two again for both data sets until either uniform agreement is found or until the pre-set cut-off limit activates and causes the CRMD 10 to output a warning. Given the fact that each additional sensor increases the chances for discrepancies, it may be advisable to increase the number of iterations Phase Three will perform when the final outcomes of Phases One and Phase Two do not match in order to fine tune the tolerance/sensitivity of the CRMD 10. Other possibilities for adjusting the sensitivity of the CRMD 10 might include processing larger data sets for increased accuracy and/or adjusting the selection criteria for determining whether a particular normalized heartbeat is indicative of instability.

A person skilled in the art field will understand that the heart rhythm analysis methods detailed above are merely illustrative and are not intended to limit the scope of this invention. These and other analysis methods will be apparent to those skilled in the art field, and any one or combination of accepted analysis techniques may be utilized within the CRMD 10 in order to detect potential arrhythmia and to warn the patient to seek medical attention. Furthermore, the specific details of the analysis techniques may be set depending upon the specific circumstances for which the CRMD 10 will be used, with such design factors as the number of different sensors used, the number of different analysis techniques used, the number of beat-to-beat heartbeat data points in a data set for analysis, the specific criteria for defining whether a particular sensed heart beat is indicative of irregularity, and the number of irregularities in a given data set or over a given period of time which is indicative of an unstable heart rhythm which may indicate a possible arrhythmia set according to particular circumstances (such as the level of accuracy desired, the sensitivity desired, the average amount of time that the analysis should take, the acceptable number of false positive results, etc.). The preferred embodiment is merely illustrative of one method for analyzing a patient's heart rhythm within the scope of the CRMD 10 device.

We claim:

1. A device comprising:

a non-invasive sensor for detecting beat-to-beat heartbeat intervals, comprised of two conductive electrodes, wherein said sensor detects beat-to-beat heartbeat intervals by sensing the electrical impulses generated by a patient's heart;

a means for storing the beat-to-beat heartbeat interval data sensed by said sensor;

an arrhythmia detection algorithm which monitors the variance in the R—R interval between heartbeats and wherein said arrhythmia detection algorithm determines a normal range of variance if the variance in the R—R interval between heartbeats is less than or equal to approximately 125 milliseconds and determines an irregular variance if the variance in the R—R interval between heartbeats is greater than approximately 125 milliseconds;

a microprocessor for executing said algorithm with the beat-to-beat heartbeat interval data sensed by said sensor, to generate a result;

an output device for conveying the results of said microprocessor's application of said algorithm to the beat-to-beat heartbeat interval data sensed by said sensor; and a power source to provide power to said microprocessor, said output device, said sensor, and said means for storing.

2. A device as in claim 1 wherein said microprocessor counts the number of irregular variances in the R—R interval between heartbeats and transmits a signal to said output device warning of a potential arrhythmia in the event that the number of irregular variances in the R—R interval between heartbeats exceeds a pre-set criteria.

3. A device comprising:

a non-invasive sensor for detecting beat-to-beat heartbeat intervals, comprised of two conductive electrodes, wherein said sensor detects beat-to-beat heartbeat intervals by sensing the electrical impulses generated by a patient's heart;

a means for storing the beat-to-beat heartbeat interval data sensed by said sensor;

an arrhythmia detection algorithm which normalizes the sensed beat-to-beat heartbeat interval data by dividing each sensed beat-to-beat heartbeat interval by only the succeeding sensed beat-to-beat interval, and which employs statistical normal distribution analysis to classify said normalized heartbeat intervals as indicative of instability and which indicates an unstable heart rhythm possibly indicative of arrhythmia in the event that the number of irregular variances in the R—R interval between heartbeats exceeds a pre-set criteria;

a microprocessor for executing said algorithm with the beat-to-beat heartbeat interval data sensed by said sensor, to generate a result;

an output device for conveying the results of said microprocessor's application of said algorithm to the beat-to-beat heartbeat interval data sensed by said sensor; and a power source to provide power to said microprocessor, said output device, said sensor, and said means for storing.

* * * * *